United States Patent [19]

Danby et al.

[11] Patent Number: 4,741,344
[45] Date of Patent: * May 3, 1988

[54] EAR CANAL ELECTRODE

[75] Inventors: Hal C. Danby, Palo Alto; Myron A. Beigler, Los Altos Hills, both of Calif.

[73] Assignee: Nicolet Instrument Corporation, Madison, Wis.

[*] Notice: The portion of the term of this patent subsequent to Nov. 18, 2003 has been disclaimed.

[21] Appl. No.: 932,007

[22] Filed: Nov. 17, 1986

Related U.S. Application Data

[63] Continuation of Ser. No. 424,387, Sep. 27, 1982, Pat. No. 4,622,975, Continuation-in-part of Ser. No. 342,490, Jan. 26, 1982, abandoned.

[51] Int. Cl.⁴ ............................................. A61B 5/04
[52] U.S. Cl. .................................... 128/642; 128/746; 128/789
[58] Field of Search ........ 128/639, 642, 746, 151–152, 128/341, 343, 9, 789; 181/129–130, 135; 381/68.6

[56] References Cited

U.S. PATENT DOCUMENTS

| Re. 26,174 | 3/1967 | Leale | 381/68.6 |
|---|---|---|---|
| Re. 29,487 | 12/1977 | Gardner, Jr. | 128/152 |
| 521,800 | 6/1894 | Leech | 128/24.1 |
| 1,684,859 | 9/1928 | Catlin | 128/789 |
| 2,934,160 | 4/1960 | Tousun | 181/130 |
| 3,303,902 | 2/1967 | Knott | 181/135 |
| 3,547,104 | 12/1970 | Buffington | 128/696 |
| 3,567,657 | 3/1971 | Lichtenstein | 252/500 |
| 3,783,201 | 1/1974 | Weiss et al. | 381/68.6 |
| 3,783,864 | 1/1974 | Moller | 128/152 |
| 3,882,848 | 5/1975 | Klar et al. | 128/746 |
| 3,935,401 | 1/1976 | Shore et al. | 181/135 |
| 3,991,755 | 11/1966 | Vernon et al. | 604/20 |
| 4,006,796 | 2/1977 | Coehorst | 181/130 |
| 4,088,133 | 5/1978 | Twentier | 128/644 |
| 4,109,648 | 8/1978 | Larke et al. | 128/639 |
| 4,114,263 | 9/1978 | Szpur | 128/641 X |
| 4,133,984 | 1/1979 | Akiyama | 381/68.6 |
| 4,166,453 | 9/1979 | McClelland | 128/639 |

FOREIGN PATENT DOCUMENTS

| 2653959 | 6/1978 | Fed. Rep. of Germany | 128/642 |
|---|---|---|---|
| 1423194 | 1/1976 | United Kingdom | 128/151 |

OTHER PUBLICATIONS

Lundborg, T. et al., "Scandinavian Auditory Supplementum", No. 13, (1981), pp. 55–64.
Erickson, D. et al., "Hearing Instruments", (1981), pp. 34–43.

Primary Examiner—Kyle L. Howell
Assistant Examiner—Angela D. Sykes
Attorney, Agent, or Firm—Isaksen, Lathrop, Esch, Hart & Clark

[57] ABSTRACT

A non-invasive, external ear canal electrode useful for transmitting sound stimulus to an ear canal and for conducting electrical signals picked up from the ear canal epidermal surface including a tube comprising electroconductive metal and having a resilient plastic foam element impregnated with an electrolytically conductive medium attached to the end to be placed in the ear.

7 Claims, 2 Drawing Sheets

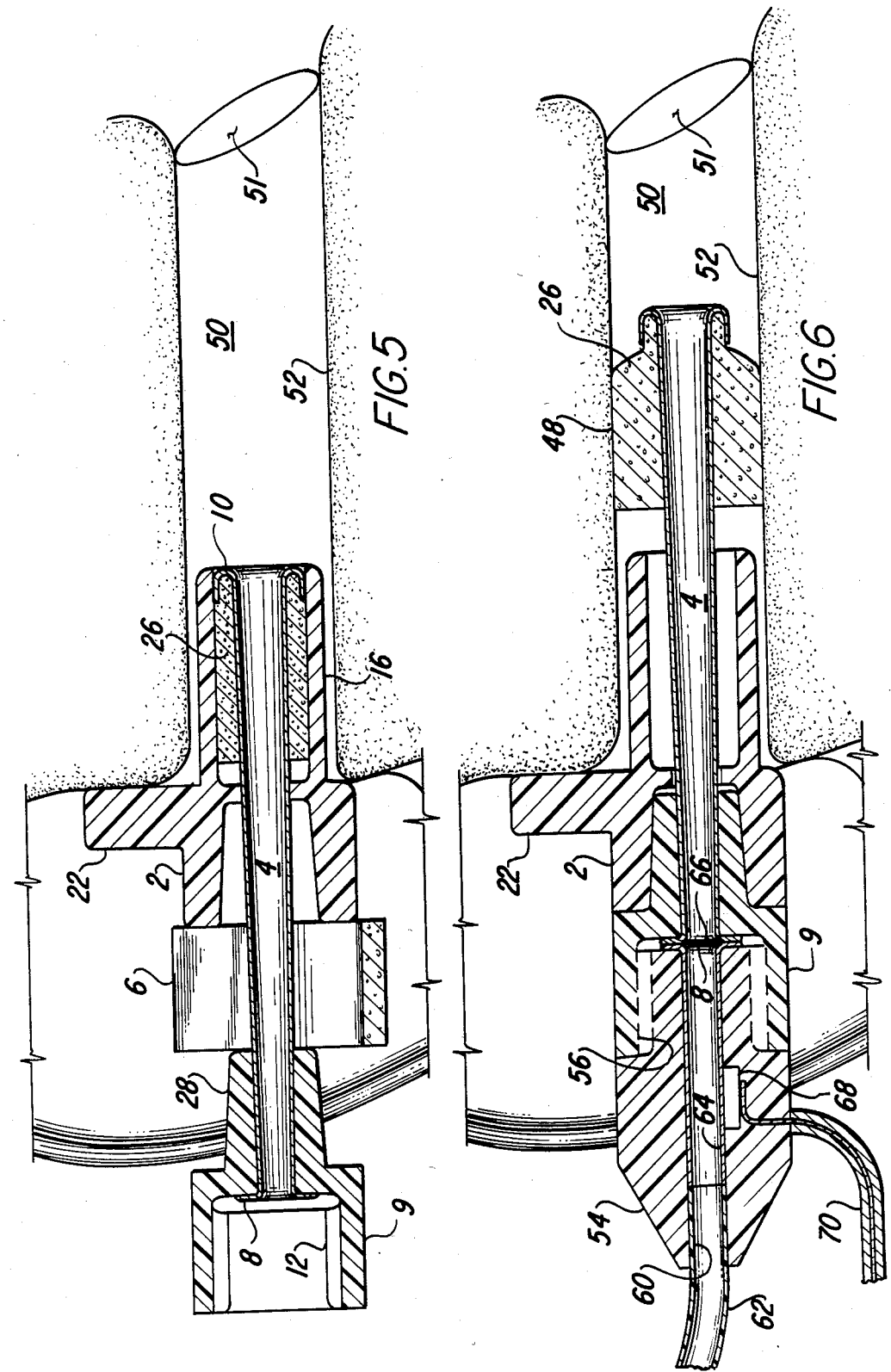

EAR CANAL ELECTRODE

RELATIONSHIP TO CO-PENDING APPLICATION

This application is a continuation of copending application Ser. No. 424,387, filed Sept. 27, 1982, now U.S. Pat. No. 4,622,975, issued Nov. 18, 1986, which is a continuation-in-part of copending application Ser. No. 342,490 filed Jan. 26, 1982, and now abandoned.

BACKGROUND OF THE INVENTION

1. Field of the Invention

Medical examinations to identify and diagnose hearing defects have historically involved physical examination of the ear canal and observing the subjective response to sound stimulus. Generally, the subjective sensitivity to volume has been routinely measured at several auditory frequencies. Most recently, the evoked action potentials resulting from auditory stimulation and auditory brainstem responses have been measured in an effort to identify more specifically the cause and degree of hearing loss and other hearing defects. Auditory brainstem response measurements involve auditory stimulation and measurement of the magnitude and response time of electrical signals originating from the otic nerve and brainstem in response to the auditory stimulus. The electrical signals are detected by using non-invasive eletrodes mounted on the skin surface.

2. Description of the Prior Art

Ear canal mounted devices for providing auditory stimuli to the ear are well known in the art. The sound is frequently transmitted to the ear through a tubular component as shown in U.S. Pat. No. Re. 26174 which is directed to a hearing aid and a method for its construction. In general, these devices are designed to provide a close or snug fit in the ear canal and may include resilient components to achieve this. U.S. Pat. No. 3,783,201 discloses a hearing aid with a flexible construction U.S. Pat. No. 4,133,984 describes a hearing aid with a flexible, expandable (inflatable) end portion. These hearing aids are designed to provide auditory stimulus but are not suitable or intended to receive electrical signals from the surface of the ear canal.

Electrodes suitable for use in conducting electrical signals from the surface of the skin are commonly used in electrocardiology measurements and the like. These electrodes are designed to have a low resistance and high sensitivity as described in U.S. Pat. Nos. 3,547,104 and 4,166,453. The latter patent describes a body electrode comprising a porous foam disc impregnated with an electrically conductive gel and other components cooperating therewith made or electrical conductive plastic. These electrodes are designated to be easily applied to a flat skin surface. They are not suitable for ear cannel insertion and are not adapted for providing any sound stimulus.

Conductive metal electrodes which penetrated the eardrum, i.e. transtympanic electrodes, have been used. They require use of an anesthetic, are painful and often result in infection. They have been used to pick up signals from close to the cochlea for increased signal strength of the first auditory action wave.

Typical electrodes designed for non-invasive external ear canal insertion for measuring auditory brainstorm responses are described in *Scandinavian Audiology Supplementum No.* 13, titled "Scandinavian Symposium or Brain Stem" edited by T. Lundborg (April 7-8, 1981). "Identification of Wave I by Means of Atraumatic Ear Canal Electrode" by Walter et al, pp 63–64 describes an electrode made of silver wire, the terminal end supporting a salt water impregnated cotton ball. "An Improved Technique for the Non-Invasive Recording of Brain-Stem Responses with a Specially Constructed Meatal Electrode" by Lang et al, pp 59–62 describe a silver wire electrode designed to be worn under earphones, the terminal end to be coated with electrode jelly. "Ear-canal Compared to Mastoid Electrode Placement in BRA" by Harder et al, pp 55–57 describes an acrylic plastic electrode with a silver element having a silver chloride surface layer embedded therein. Electrode paste is applied to the ear canal before inserting the electrode. These devices do not have the construction of the ear electrodes of this invention and do not provide the low resistance and high sensitivity thereof. Also, these devices have no means for providing auditory stimuli. In each referenced system, the auditory stimuli is provided through devices not physically associated with the ear electrode. An even greater limitation of all of the invasive and non-invasive electrodes of the prior art has been the requirement that a physician make the insertion because of the potential for inadvertent penetration of the eardrum.

OBJECTS AND SUMMARY OF THE INVENTION

It is an object of this invention to provide a non-invasive external ear canal electrode with reduced electrical resistance and greater electrical sensitivity.

It is a further object of this invention to provide a safe, disposable ear canal electrode which can be simply and inexpensively manufactured and which can be easily and safely inserted by medical assistants with a minimum amount of training in ear anatomy without the risk of eardrum damage due to inadvertent penetration thereof.

In summary, the safe and non-invasive external ear canal electrode of this invention comprises a tube of electro-conductive material for conducting electrical signals picked up from the skin surface and for transmitting sound stimulus to the human ear canal surface. An electro-conductive, resilient, open-celled, plastic foam member is mounted on the end of the tube which is to be placed in the ear canal, and it is designated to contact the epidermal skin surface of the ear canal and pick up and conduct electrical signals therefrom to the tube. In the preferred embodiments of this invention, the tube is made of a suitable metal, has a metal coating or outer metal layer, or is a conductive metal-filled plastic with silver being a particularly preferred metal; the plastic foam member is an annular element surrounding the distal end of the tube; and the plastic foam is a continuously connected cell foam impregnated with an electrolytically conductive medium.

In a still further embodiment, the annular plastic foam member is compressively enclosed in a concentric outer insertion tube designed for insertion into the ear canal. This tube forms a moisture-tight seal with the end of the tube so as to prevent evaporation of water from the electro-conductive medium with which the plastic foam member is impregnated. When the insertion tube is retracted from around the plastic foam, the foam expands within the ear canal to effect a positive and electrically conductive skin contact. The insertion tube has a guard or stop portion which limits the insertion distance in the ear canal short of the ear drum.

BRIEF DESCRIPTION OF THE DRAWINGS

FIG. 5 is a side-sectional view of the ear canal electrode of this invention in the initial insertion position in the ear canal.

FIG. 6 is a side-sectional view of the ear canal electrode of this invention after removal of the retaining clip, insertion of the electrode to the final insertion position, and expansion of the plastic foam element.

DETAILED DESCRIPTION OF THE INVENTION

In an effort to diagnose the cause of partial and total hearing loss and other hearing defects, techniques have been developed around measurements of the auditory brainstorm response (ABR) and electrocochleography (ECoG). The early techniques involved measuring electrical potential variations on the scalp surface within the first 10 milliseconds following auditory stimulation. The auditory system was stimulated with sound, usually in the form of short clicks or bursts of selected wave shape, amplitude and frequency. The resulting electrical field potentials generated by synoptic events and membrane potential fluctuations along the central auditory pathway, and in particular in the nerve cell layers of the deep brainstem structures, were transmitted through the volume (brain tissue, bone and extracellular fluid) of electrically conducting medium as potentials detected using the scalp electrodes. The amplitude and latency of the electrical potentials have been correlated with specific sites along the auditory nervous system pathway. Potentials originating from the cochlear transducer and auditory brainstem are the most significant. Irregularities in the amplitude and latency of the characteristic waves can be used to identify the degree and specific cause of a hearing deficiency.

A number of factors have limited the use of ABR and ECoG. Originally sharp clicks are distorted in passage and transmission in the ear passageways. The stimulus does not stimulate all of the cochlear hair cells simultaneously. Electrical potentials observed are very weak and often ambiguous due to distortion introduced by passage through the body structure and from background noise. Placements of electrodes in the ear canal and through the ear drum were found to reduce some distortion and give increased sensitivity. The surface of the ear canal is adjacent to dense, conductive bone, and electrical potentials measured on the ear canal surface have been transmitted through less insulative tissue and fluid. It was found that correctly designed metal, non-invasive ear canal surface electrodes can obtain signals equivalent to transtympanic electrodes. However, background noise was even greater in the ear with many non-invasive electrodes because of the configuration of the ear canal surface. Only with highly skilled investigators, elaborate skin surface preparation, expansion of the canal entrance with a speculum and insertion of electrodes with microsurgical forceps has resistance been measured below 10 Kohms.

The non-invasive external ear canal electrode of this invention, as set forth in more detail hereinafter, can be applied in a routine manner by ordinary, medically trained technicians to give an electrical resistance as low as one Kohm. This device also provides that sound is transmitted through an integral, acoustic horn with minimal distortion.

Figure 1:
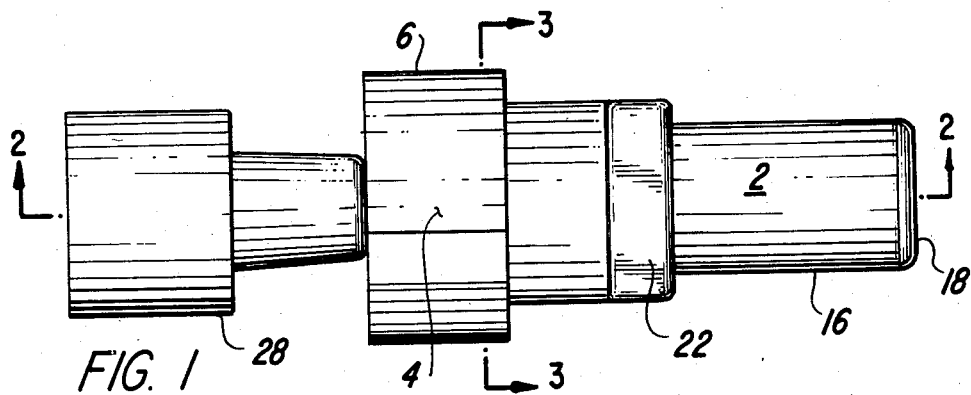
FIG. 1 is directed to a top view of the non-invasive external ear canal electrode, fully assembled prior to use.

Referring to FIG. 1, a top view of the ear electrode of this invention is shown, assembled for insertion in the ear canal. The insertion tube 2, mounted on the tubular electrode 4, is held in position by removable clip member 6.

Figure 2:
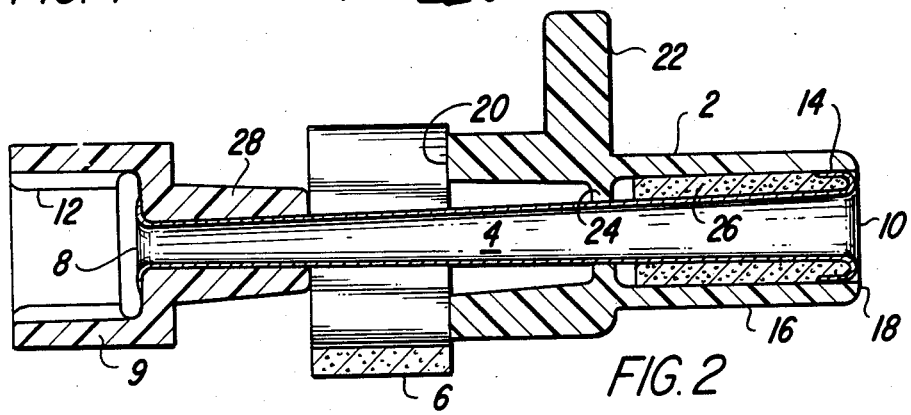
FIG. 2 shows a cross-sectional view of the ear canal electrode of this invention taken along the line A—A in FIG. 1.

The side view, in a cross-section taken along line A—A in FIG. 1, is shown in FIG. 2. The tubular electrode 4 has a proximal end 8 and a distal end 10. The proximal end 8 is shown mounted in a cup-shaped recess connector 9 having inner locking threads 12 for engaging a mating element on a sound generator described hereinafter with regard to FIG. 6. The tubular electrode 4 has a circular cross-section, the inner diameter thereof increasing as the distal end is approached to give the tapered or flared configuration of an acoustical horn. This configuration delivers sound introduced at the proximal end 8 to the ear canal with minimal distortion, permitting auditory stimulation with sharp, crisply configured clicks. The distal end 10 is folded back on itself to form a clamping portion 14. The cup-shaped connector is preferably made of non-conductive plastic such as polyvinyl chloride, polyethylene or the like. The tubular electrode 4 can be of any electrically conducting, physiologically inert material which electrochemically reacts with the electrolytically conductive medium described hereinafter. It can be made of metal, have a metal coating, or be filled with an electro-conductive metal. Aluminum, zinc, chromium, iron, cadmium, nickel, lead, lead-mercury amalgan, platinum, silver, copper, mercury and gold can be used, for example. Preferred metals are stable in aqueous chloride solutions and include stainless steel and silver. Optimum metals provide a minimum potential difference between electrode pairs. Silver electrodes have one of the smallest potential differences between electrode pairs and provide a minimum noise. This noise can be reduced further by "chloriding" the surface of the electrode which contacts the electrolytically conductive gel. A silver electrode can be chlorided by placing it under a positive voltage in an aqueous sodium chloride solution yielding a surface composition of silver-silver chloride. Because this surface is easily damaged and silver chloride, being light sensitive, can introduce electrical noise in response to light fluctuations, the chlorided silver surface electrodes are not always optimum. Stainless steel electrodes are also highly suitable.

The insertion tube 2 has an outer cylindrical portion 16 designed for insertion into the ear and with a rounded, smooth leading edge 18. Between the proximate end 20 and the leading edge 18 is a flanged portion or guard 22 which functions as a stop, limiting the depth of tube insertion into the ear canal and thereby eliminating risk of eardrum damage by inadvertent penetration. The insertion tube has a circular opening 24 through which the electrode tube 4 passes in sliding engagement. The insertion tube 2 can be made of plastic (as illustrated), metal or cellulosic material such a laminated paper or compressed fibers which can function as a moisture barrier.

The cylindrical portion 16 of the insertion tube surrounds and confines the resilient plastic foam member 26 during insertion. The insertion tube edge 18 forms a moisture-tight seal with the folded back portion 14, and the opening 24 forms a moisture-tight seal with the outer surface of the tubular electrode 4. This prevents evaporation of water or other solvents which may be present in a gel coating on the plastic foam member 26.

Figure 3:
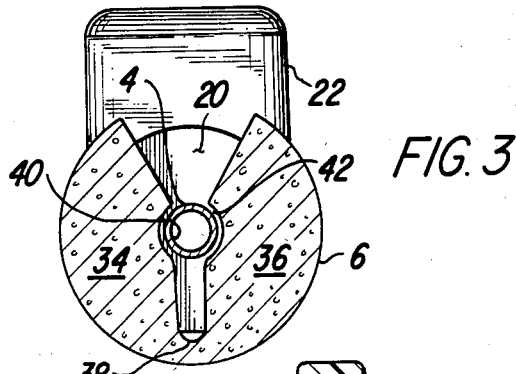
FIG. 3 is a cross-sectional view of the fully assembled ear canal electrode of this invention, prior to use, taken along line C—C in FIG. 1.

The insertion tube 2 is held in position enclosing the plastic foam members 26 by the clip member 6. FIG. 3 is a cross-sectional view taken along the line C—C in FIG. 1 and shows the clip member 6 in more detail. Clip member 6 is shown as a plastic member comprising two halves 34 and 36 and an integral, connecting hinge portion 38. The clip member halves 34 and 36 have an inner surface of cylindrical contour 40 matching the shape of the outer surface 42 of the tubular electrode 4. Clip member 6 can be made of a plastic foam as shown, polyethylene, or other plastic or it can be replaced with a clip made of metal, cardboard or other solid material. Clip member 6 can be easily removed by spreading the two halves 34 and 36 apart and disengaging outer surface 42 of the electrode tube 4.

Figure 4:
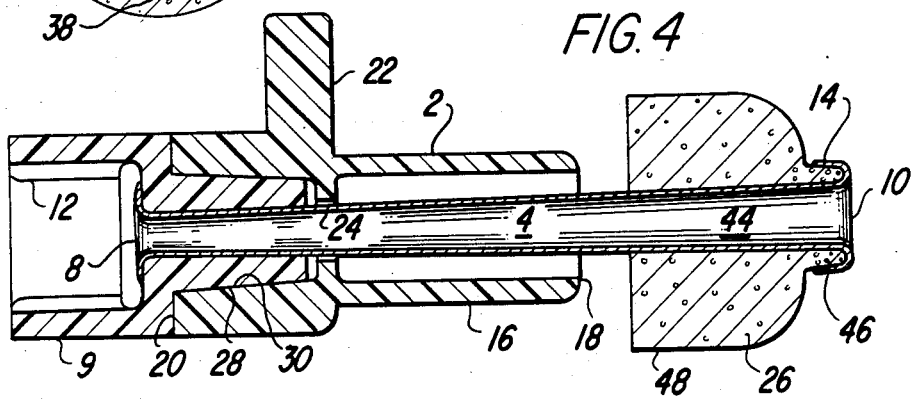
FIG. 4 is a cross-sectional view of the ear canal electrode of this invention showing the plastic foam expansion after the insertion tube retraction.

FIG. 4 shows a top cross-sectional view taken through the central axis of the ear electrode of this invention showing the device with the clip member 6 removed and the insesrtion tube 2 retracted. The connector 9 has a tubular portion 28 which frictionally engages recess portion 30 of the insertion tube 2 when it is retracted, retaining the insertion tube in the retracted position.

Since this is shown outside of the ear canal environment, the plastic foam element 26 is shown in the relaxed, fully extended condition. The plastic foam element is preferably of cylindrical shape, with a diameter larger than the ear canal and with a cylindrical passageway 44 through which the tubular electrode 4 protrudes. The end 46 of the plastic foam proximate the distal end 10 is held in place by the clamping portion 14 of the tubular electrode 4, crimped and pinching the end of the plastic foam in tight compression. Alternatively, a claming ring member can be used.

The plastic foam member 26 can be made from any resilient, open-celled plastic foam material. It is preferably made from a continuously connecting cell material such as the very highly expanded product, FILTER FOAM made of polyurethane. The foam preferably contains or is impregnated with an electrolytically conductive medium which can be a liquid, gel, jelly, or other dispersion or suspension having good electro-conductive properties and which electrochemically reacts with the conductive metal of the tubular electrode 4. For example, the electrolytically conductive medium can be an electrically conductive emulsion comprising an emulsified material dispersed in an aqueous solution of an electrolytically conductive salt such as sodium chloride, potassium chloride or sodium sulfate and a surfactant dispersing agent. It can also be an electrically conducting jelly comprising an aqueous sodium chloride solution phase gelled with conventional gelling agents such as sodium carboxymethylcellulose and having as the conductive salt, potassium chloride, sodium sulfate, potassium sulfate, sodium bromide, potassium bromide, sodium nitrate, ammonium fluoride, ammonium bromide, ammonium nitrate, ammonium sulfate, and the like.

Referring to FIGS. 5 and 6, cross-sectional views of the ear electrode of this invention in the initial and final insertion positions in the ear canal are shown.

In FIG. 5, the flange portion 22 is shown abutting the external ear surface, limiting the depth of travel of the device in the ear canal 50 during the initial insertion, and preventing contact with eardrum 51. The cylindrical portion 16 of the insertion tube 2 is in contact with the ear canal epidermal surface 52. The insertion tube 2 has been held in position during insertion by clip member 6. The plastic foam member 26 is still enclosed by the injection tube. Because the leading edge 18 is rounded and smooth, damage to the ear canal epidermal tissues is avoided during insertion.

FIG. 6 shows the ear electrode of this invention after the clip member 6 has been removed and the tubular element 4 has been inserted to the final position. This leaves the insertion tube 2 retracted from around the extended foam member 26. The plastic foam member 26 has expanded to positively engage the ear canal epidermal surface 52. A thin layer of excess electrolytically conductive medium on the outer surface 48 of the plastic foam insures good electrical contact with the skin surface and minimal electrical resistance. An excess can be applied to the ear surface before the electrode is inserted. However, the plastic foam is preferably impregnated with an excess of the medium. Because of the moisture-tight enclosure provided by the insertion tube 2, the evaporation of solvent from the medium is prevented, and the ear electrode is always ready for insertion, even after prolonged storage.

Because the flange 22 limits the distance of movement of the tubular electrode 4, risk of inadvertent contact or penetration of the eardrum 51 is completely eliminated, making it possible for routine insertion by ordinary medical testing assistants without specialized training.

The connector 9 of the tubular electrode 4 engages the auditory signal generator connector 54. The auditory signal generator source has a connecting element 56 which has a configuration which mates with the locking threads 12 to hold the respective elements together.

Connector 54 is provided with a recess 60 which receives and engages tube 64. Tube 64 is preferably made of the same metal as the tubular electrode 4 so that bimetal junction impedance is minimized. It has an end 66 which makes electrical contact with the proximate end 8 or the tubular electrode 4. Wire 70 which transmits electrical signals from tube 64 to an auditory brainstem response analyzer (not shown), is connected to tube 64 by junction 68.

The auditory signal generator and its associated magnetic field shielding can be of any standard type suitable for providing the auditory stimulation required for auditory brainstem response. The auditory sound generator is of standard contruction well known in the art and is not an essential part of this invention.

A description of the procedures for measuring and analyzing auditory brainstem response is provided by "Physiological Mechanisms and Auditory Brainstem Evoked Response" by E. Borg, pp. 11–22 in the *Scandinavian Audiology Supplementum No.* 13, supra and "Auditory Evoked Potential Instrumentation: How to Choose", by Erickson et al, *Hearing Instruments*, Volume 32, No. 8, 1981, pp. 31–43, the entire contents of which are incorporated by reference. Included in the latter article is a description of the equipment currently available for making auditory brainstem response test analysis and ancillary equipment such as auditory signal generators.

A typical commercial auditory evoked potential system consists of units for stimulus presentation, signal detection, amplification and filtering, signal averaging, displaying data, hard copying the data record and mass storage. The standard stimulus is a short-duration click produced by applying a square wave to the auditory signal generator with repetitions as high as 80 clicks per second. The evoked potential signal voltages detected by the electrode of this invention are extremely small in amplitude, and extraneous noise introduced by amplification is removed by averaging. Filter settings are provided for optimum rejection of energy outside the frequency range of the evoked potential being recorded. The signal averager controls and senses the presentation of stimuli, collects the incoming signal and processes the data to form an averaged wave form. A display provides the operator with information regarding the averaged wave form and the input signal derived from the averaged signal. This can be a normalized display in which the summed data is divided by the number of repetitions. A means for producing a hard copy of the data is convenient, and a digital mass data storage capability is important.

The growing interest in the auditory, evoked potential testing can be traced to the discovery of the auditory brainstem response recorded non-invasively from the human scalp. Subsequent research developed this test to provide a useful and versatile technique for evaluating hearing. It provides a means for examining patients who are difficult to test by behaviour means, efficiently discriminating between conductive and cochlear hearing disorders and differentiating peripheral and central pathology. Cochlear potentials of elevated magnitude indicate pressure in the inner ear. In some cases it can also reveal clinically asymptomatic lesions of the central pathways. The principal limitations derive from the high noise level in the electrical signal received from the skin surface. This noise level constitutes a serious impediment to full development of this testing means. Since the electrical signal being detected is less than one microvolt in amplitude, any extraneous noise introduced by amplification creates serious problems. Furthermore, resistance introduced by the electrode component of the assembly and resulting from a high resistance at the skin-electrode interface greatly reduces sensitivity.

The ear electrode of this invention provides as greatly reduced skin-ear surface resistance and far greater sensitivity. To minimize electrical resistance and impendance, it is important to employ an electrolytically conductive gel impregnated plastic foam. The gel provides an optimum conduction between the skin surface 52 and the conductive tubular electrode 4. It is also important to have a single metal conductor (no bimetal junction) between the electrodconductive gel and the electrical junction 68. The normally operating resistance has thus been reduced below 2 Kohm.

A high degree of safety and ease of insertion has been achieved. risk of eardrum penetration has been eliminated even when the electrode is inserted by medical assistants with no special training in ear anatomy. The special guard 22 limits insertion distance to a depth short of the eardrum.

The invention claimed is:

1. A non-invasive external ear canal electrode comprising a tubular electrode means of electro-conductive material for conducting electrical signals picked up from the ear canal surface and for transmitting a sound stimulus to an ear canal, said electrode means having a proximal end and a distal end, the distal end having mounted thereon an electro-conductive, resilient, annular plastic foam means through which the electrode means protrudes for contacting the skin surface of the ear canal and picking up and conducting electrical signals therefrom.

2. The ear canal electrode of claim 1 wherein the tubular electrode means comprises metal.

3. The ear canal electrode of claim 2 wherein the metal consists essentially of silver or stainless steel.

4. The ear canal electrode of claim 1 wherein the plastic foam means is a open-cell plastic foam.

5. The ear canal electrode of claim 4 wherein the plastic foam means is impregnated with an electrolytically conductive medium.

6. The ear canal electrode of claim 5 wherein a portion of the plastic foam means proximate the distal end of the electrode means is compressibly held against the electrode means by an annular clamping means.

7. The ear canal electrode of claim 1 wherein the tubular electrode means is an acoustical horn.

* * * * *

UNITED STATES PATENT AND TRADEMARK OFFICE
CERTIFICATE OF CORRECTION

PATENT NO. : 4,741,344

DATED : May 3, 1988

INVENTOR(S) : Hal C. Danby, et al.

It is certified that error appears in the above-identified patent and that said Letters Patent are hereby corrected as shown below:

Col. 1, line 53, "or" should be --of--.

Col. 1, line 56, "cannel" should be --canal--.

Col. 5, line 31, "insesrtion" should be --insertion--.

Col. 5, line 46, "claming" shouldbe --clamping--.

Col. 8, line 6, "impendance" should be --impedance--.

Signed and Sealed this

Sixth Day of September, 1988

Attest:

DONALD J. QUIGG

Attesting Officer     Commissioner of Patents and Trademarks